US00PP26505P3

(12) United States Plant Patent
Westphal

(10) Patent No.: US PP26,505 P3
(45) Date of Patent: Mar. 15, 2016

(54) *CLEMATIS* PLANT NAMED 'BLUE JEANNE'

(50) Latin Name: *Clematis lanuginosa*
Varietal Denomination: Blue Jeanne

(71) Applicant: Friedrich Manfred Westphal, Prisdorf (DE)

(72) Inventor: Friedrich Manfred Westphal, Prisdorf (DE)

( * ) Notice: Subject to any disclaimer, the term of this patent is extended or adjusted under 35 U.S.C. 154(b) by 105 days.

(21) Appl. No.: 14/120,187

(22) Filed: May 1, 2014

(65) Prior Publication Data

US 2015/0319897 P1 Nov. 5, 2015

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Cassandra Bright

(57) ABSTRACT

A new and distinct *Clematis* cultivar named 'Blue Jeanne' is disclosed, characterized by a long flowering period and distinctively clear blue flowers. The new cultivar is a *Clematis*, suitable for ornamental garden purposes.

1 Drawing Sheet

Latin name of the genus and species: *Clematis lanuginosa*.
Variety denomination: 'BLUE JEANNE'.

BACKGROUND OF THE INVENTION

The new cultivar is a product of a planned breeding program conducted by the inventor during 2009. May of 2009, the inventor, Friedrich Manfred Westphal, a citizen of Germany, made an open pollination of the seed parent *Clematis lanuginosa* 'Fujimusume', unpatented, with an assortment of *Clematis lanuginosa* varieties. Therefore, the true pollen parent is unknown. Seeds originating from this crossing were planted out, and the new variety was selected during August of 2009. All work was conducted at a commercial nursery in Prisdorf, Germany.

The inventor first propagated 'Blue Jeanne' by vegetative cuttings at the commercial nursery in Prisdorf, Germany in April of 2010. Subsequent generations have shown that the unique features of this cultivar are stable and reproduced true to type.

SUMMARY OF THE INVENTION

The cultivar 'Blue Jeanne' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Blue Jeanne' These characteristics in combination distinguish 'Blue Jeanne' as a new and distinct *Clematis* cultivar:

1. Clear blue flower color.
2. Long flowering period.

COMPARISON TO PARENT VARIETY

Plants of the new cultivar 'Blue Jeanne' are similar to plants of the seed parent; *Clematis lanuginosa* 'Fujimusume' in most horticultural characteristics, however, plants of the new cultivar 'Blue Jeanne' are more vigorous, achieve a larger mature size and have a different flower period. Additionally, flowers of the new variety have a more true blue color and longer internodes.

COMMERCIAL COMPARISON

'Blue Jeanne' can be compared to the commercial variety 'Elsa Spath', unpatented. The varieties are similar in many horticultural characteristics. The new variety, however, produces a flower of a much clearer blue color, and blooms over a longer period of time.

'Blue Jeanne' can also be compared to *Clematis* 'Blue Pillar', unpatented. The varieties are similar in many horticultural characteristics. The new variety, however, produces a flower of a much clearer blue color, begins blooming earlier, and blooms over a longer period of time.

BRIEF DESCRIPTION OF THE PHOTOGRAPH

The accompanying photograph in FIG. 1 illustrates in full color a close up of typical foliage and flowers of 'Blue Jeanne' grown outdoors in Germany. The plant is approximately 1 year old, and is planted in the ground.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Blue Jeanne' plants grown in a greenhouse in Prijsdorf, Germany. Plants are approximately 1 year old, in a 1 liter nursery container. The greenhouse is unheated and unshaded.

Temperatures ranged from 2° C. to 20° C. at night to 5° C. to 35° C. during the day. Measurements and numerical values represent averages of typical plant types.

Botanical classification: *Clematis lanuginose* 'Blue Jeanne'.

PROPAGATION

Time to rooting:

*Initiation.*—Approximately 30 days in the Summer at approximately 24° C.

*Rooted cuttings production.*—Approximately 65 days in the Summer at approximately 20° C. to 26° C.

Root description: Fine, fibrous.

PLANT

Growth habit: Climbing vine.

Height: Approximately 220 cm to 270 cm, measured from the soil line of the pot after approximately 1 year.

Plant spread: Approximately 60 cm after approximately 1 year.

Growth rate: During active growing season in Spring, approximately 40 to 50 cm per month.

Branching characteristics: One main stem, and 1 to 5 lateral branches, typically given a pinch.

Length of main stem: Approximately 220 cm.

Diameter of main stem: Approximately 0.8 cm.

Main stem color: Near RHS Green 137B, flushed Greyed-Purple N187A.

Main stem texture: Slightly pubescent.

Internode length: Varies from 8 to 15 cm.

Strength: Strong, flexible, semi-woody.

FOLIAGE

Leaf:

*Type.*—Simple.

*Arrangement.*—Opposite.

*Leaves per lateral branch.*—Average 3.

*Average length.*—Approximately 4 to 5 cm.

*Average width.*—Approximately 3.0 to 4.0 cm.

*Shape of blade.*—Oblong.

*Apex.*—Acute.

*Base.*—Cordate.

*Margin.*—Entire.

*Texture of top surface.*—Smooth.

*Texture of bottom surface.*—Smooth.

*Color.*—Young foliage upper side: Near RHS Green 137C. Young foliage under side: Near RHS Green 137B. Mature foliage upper side: Near RHS Green 137A. Mature foliage under side: Near RHS Green 137B.

*Venation.*—Type: Pinnate. Venation color upper side: Near RHS Green 137B. Venation color under side: Near RHS Green 137A.

*Petiole.*—Average Length: Approximately 4 to 5 cm. Color: Near RHS Green 137A, flushed Greyed-Purple 187A. Diameter: Approximately 0.2 cm. Texture: Smooth.

FLOWER

Bloom period:

*Natural season.*—Spring through Summer.

Inflorescence type and habit: Single, axillary; flowers facing outward.

Flower longevity on plant: Approximately 10 days, after fully opened. Self-cleaning.

Quantity of flowers: Approximately 20 open flowers at one time.

Inflorescence size:

*Diameter.*—Approximately 10 to 14 cm.

*Depth.*—Approximately 2.0 cm.

Corolla:

*Tepal arrangement.*—Single whorl, slightly overlapping.

*Quantity.*—Approximately 6 to 8 per flower.

*Size.*—Length: Approximately 4 to 5 cm. Width: Approximately 2.0 to 2.5 cm.

*Margin.*—Entire, very slightly undulating.

*Apex.*—Acute.

*Base.*—Truncate.

*Texture.*—Smooth, velvety.

Color:

*Tepals.*—When opening: Upper surface: Near RHS Blue 100B, center near Blue 101D. Lower surface: Near RHS Blue 100B. Fully opened: Upper surface: Near RHS Blue 101B, center near Blue 100D. Lower surface: Near RHS Blue 101B, center streak near Blue 101D. Ageing: Upper Surface: Near RHS Blue 100B, center near Blue 101D. Lower Surface: Near RHS Blue 100B, center near Blue 101D.

Bud:

*Shape.*—Ovate.

*Length.*—Approximately 2 to 5 cm.

*Diameter.*—Approximately 1.5 to 2.5 cm.

*Color.*—Near RHS Blue 100B.

Pedicels:

*Length.*—Approximately 4 to 8 cm.

*Width.*—Approximately 0.3 cm.

*Angle.*—Average 80°.

*Strength.*—Strong, flexible.

*Color.*—Near RHS Greyed-Purple 186B.

Fragrance: None.

REPRODUCTIVE ORGANS

Stamens:

*Number.*—Approximately 0 to 100 per flower.

*Anther length.*—0.8 cm 1.2 cm.

*Anther color.*—Near RHS Yellow-White 158A.

*Anther shape.*—Oblong.

*Pollen quantity.*—Not observed to date.

*Filament length.*—Approximately 1.2 to 2.0 cm.

*Filament aspect.*—Straight.

*Filament color.*—Near RHS White N155A.

Pistil:

*Number.*—Approximately 50 to 60 per flower.

*Length.*—Approximately 0.8 cm.

*Style color.*—Near RHS Red-Purple 70B.

*Style length.*—Approximately 0.7 cm.

*Stigma.*—Shape: Linear. Color: Near RHS White N155A.

OTHER CHARACTERISTICS

Seeds and fruits: Not observed to date.

Disease/pest resistance: Neither resistance nor susceptibility to pathogens and pests common to *Clematis* have been observed.

Temperature tolerance: Tolerates temperatures from approximately −20° C. to 45° C.

What is claimed is:

1. A new and distinct cultivar of *Clematis* plant named 'Blue Jeanne' as herein illustrated and described.

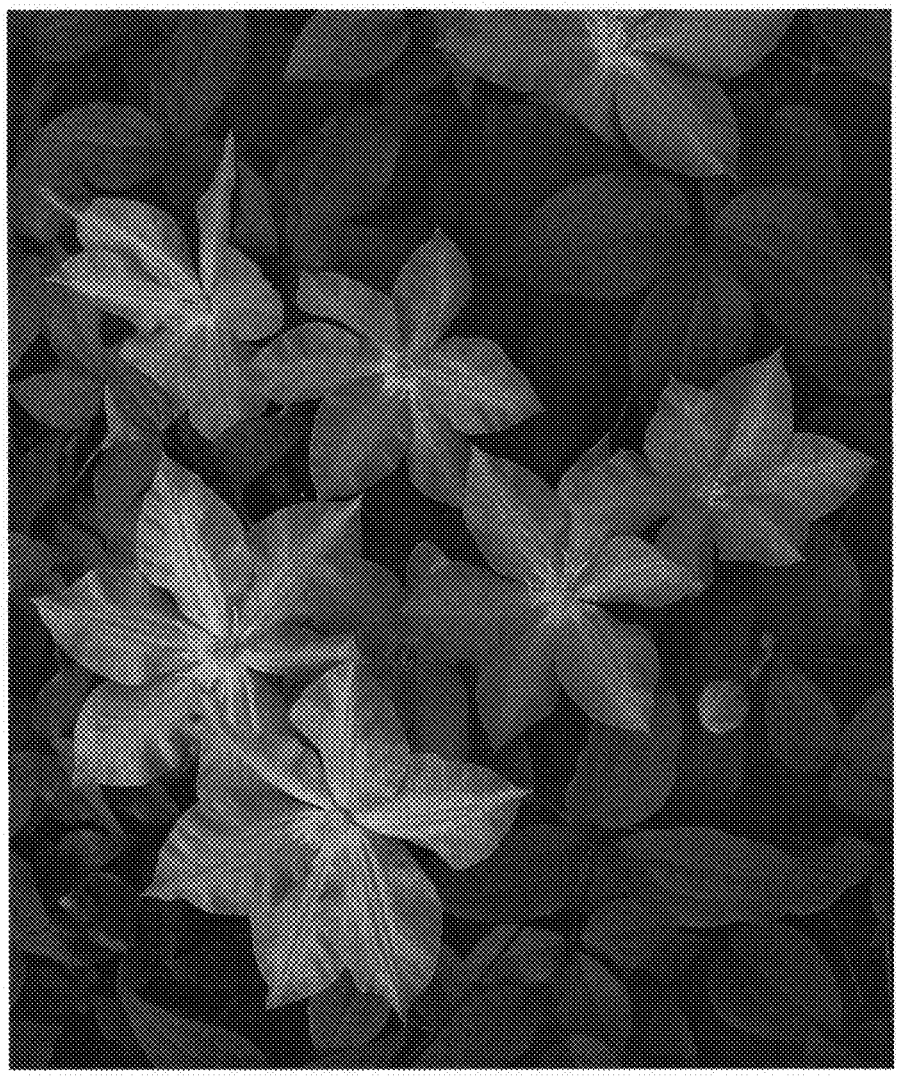

* * * * *